US006150366A

United States Patent [19]

Arenson et al.

[11] Patent Number: 6,150,366

[45] Date of Patent: Nov. 21, 2000

[54] ZIPRASIDONE FORMULATIONS

[75] Inventors: Daniel R. Arenson, East Lyme; Frank Robert Busch, Gales Ferry; Angela G. Hausberger, East Lyme; Bijan Rasadi, Groton, all of Conn.

[73] Assignee: Pfizer Inc., New York, N.Y.

[21] Appl. No.: 09/320,985

[22] Filed: May 27, 1999

Related U.S. Application Data

[60] Provisional application No. 60/089,229, Jun. 15, 1998.

[51] Int. Cl.$^{7}$ ...................... A61K 31/495; C07D 417/14

[52] U.S. Cl. .......................... 514/253; 514/254; 544/368

[58] Field of Search .................................. 514/253, 254; 544/368

[56] References Cited

U.S. PATENT DOCUMENTS

| | | | |
|---|---|---|---|
| 4,831,031 | 5/1989 | Lowe, III et al. | 514/254 |
| 4,883,795 | 11/1989 | Lowe, III et al. | 514/253 |
| 5,206,366 | 4/1993 | Bowles et al. | 544/368 |
| 5,264,446 | 11/1993 | Hegasy et al. | 514/356 |
| 5,312,925 | 5/1994 | Allen et al. | 544/368 |
| 5,338,846 | 8/1994 | Busch et al. | 544/368 |
| 5,359,068 | 10/1994 | Urban | 544/368 |
| 5,935,960 | 8/1999 | Walinsky et al. | 514/253 |

FOREIGN PATENT DOCUMENTS

| | | | |
|---|---|---|---|
| 0281309 | 9/1988 | European Pat. Off. | C07D 263/58 |
| 0548635 | 12/1992 | European Pat. Off. | A61K 31/40 |
| 0586191 | 3/1994 | European Pat. Off. | C07D 417/12 |
| 0901786 | 3/1999 | European Pat. Off. | A61K 9/14 |

*Primary Examiner*—Shep K. Rose
*Attorney, Agent, or Firm*—Peter C. Richardson; Gregg C. Benson; James T. Jones

[57] ABSTRACT

Compositions comprising crystalline ziprasidone free base or crystalline ziprasidone hydrochloride particles having a mean particle size less than 85 μm, and a pharmaceutically acceptable carrier, are substantially bioequivalent and can be used to treat psychoses such as schizophrenia.

34 Claims, No Drawings

ZIPRASIDONE FORMULATIONS

This application is filled claiming priority from co-pending Provisional Application No. 60/089,229 filed Jun. 15, 1998.

FIELD OF THE INVENTION

This invention relates to a composition of matter which is a pharmaceutical formulation of ziprasidone comprising crystalline ziprasidone particles having a maximum size cutoff, and to a method of treating a psychosis with such a formulation.

BACKGROUND OF THE INVENTION

Ziprasidone is a known compound having the structure:

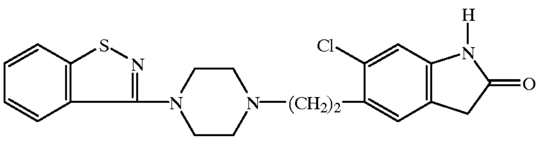

It is disclosed in U.S. Pat. Nos. 4,831,031 and 5,312,925, both of which are herein incorporated by reference in their entirety, has utility as a neuroleptic, and is thus useful, inter alia, as an antipsychotic. It is typically administered as the hydrochloride acid addition salt. The hydrochloride salt is advantageous in that it is a high permeability drug, a factor which favorably affects bioavailability. The hydrochloride salt does, however, possess relatively poor aqueous solubility, a factor which unfavorably affects bioavailability.

Low solubility compounds can be problematic in the pharmaceutical arts from a formulations perspective. Typical approaches can involve (1) using particular formulations excipients which increase solubility, for example surfactants, and/or (2) formulating the drug in a small particle size, thereby increasing the surface area of the drug to facilitate more rapid dissolution. The latter method can present difficult and expensive formulation and quality control challenges, however.

SUMMARY OF THE INVENTION

It has now been determined that compositions comprising crystalline ziprasidone free base or ziprasidone hydrochloride (herein sometimes collectively referred to as "ziprasidone" for convenience) having a mean particle size equal to or less than about 85 μm exhibit good dissolution properties at physiologic pH. Surprisingly, formulations comprising particles of ziprasidone free base or ziprasidone hydrochloride equal to or less than about 85 μm are substantially bioequivalent, meaning that, whatever the factors are that affect the bioequivalence of ziprasidone, they are largely independent of particle size below about 85 μm. Accordingly, the invention provides a pharmaceutical composition comprising crystalline ziprasidone free base or crystalline ziprasidone hydrochloride particles having a mean particle size equal to or less than about 85 μm as measured by Malvern light scattering, and a pharmaceutically acceptable diluent or carrier. It is preferred that the ziprasidone particles in the composition have a $D_{90}$ not exceeding 170 μm. It is noted the notation $D_x$ means that X% of the particles have a diameter less than a specified diameter D. Thus a $D_{90}$ of 170 μm means that 90% of the particles in a ziprasidone composition preferably have a diameter less than 170 μm.

A preferred mean particle size of ziprasidone particles is equal to or less than 50 μm. The range of mean particle sizes preferred for use in the invention is 2 to 50 μm, more preferably 5 to 50 μm, even more preferably 5 to 40 μm, and most preferably 5 to 30 μm. The particle sizes stipulated herein and in the claims refer to particle sizes determined with Malvern light scattering.

The invention further provides a method of treating a psychosis, comprising administering to a patient in need of such treatment an effective amount of a composition comprising crystalline ziprasidone free base or crystalline ziprasidone hydrochloride particles having a mean particle size equal to or less than about 85 μm as measured by Malvern light scattering, and a pharmaceutically acceptable carrier. Ziprasidone hydrochloride can be used in any active crystalline form, although ziprasidone hydrochloride monohydrate is preferred.

The formulations of this invention are advantageous because, inter alia, as noted above, they exhibit good dissolution properties at physiologic pH. The invention is surprising in this respect, however, in that the rate of dissolution in vitro does not correlate with particle size. That is, one would expect dissolution rate for a relatively low solubility drug to increase as particle size decreases and/or surface area increases. It has surprisingly been found, however, that ziprasidone dissolution rate in aqueous media, at least at or below 85 μm, does not vary substantially with particle size, and therefore appears to be largely independent of it. Thus ziprasidone free base or ziprasidone hydrochloride can be formulated in a composition having a reasonable particle size which is easily manageable using conventional formulations methodology and equipment, it not being necessary to use extreme measures or specialized technology to achieve and maintain relatively tiny particles to facilitate dissolution.

Formulations according to this invention, when dissolution tested in vitro preferably exhibit the following dissolution criteria. That is, the formulation exhibits dissolution properties such that, when an amount of the formulation equivalent to 100 mgA ("mgA" being an abbreviation designating active ziprasidone in the form of the free base, molecular weight 412.9) or less of active ziprasidone (100 mgA as free base being equivalent to 113.2 mg as ziprasidone hydrochloride monohydrate) is placed in a USP-2 apparatus containing 900 ml of 0.05 M $NaH_2PO_4$ buffer, adjusted to pH 7.5, containing 2% (w/w) sodium dodecyl sulfate, the apparatus being equipped with paddles stirring at 75 rpm, at least 70% of the ziprasidone free base or hydrochloride therein dissolves within 45 minutes. Usually the test result is established as an average for a predetermined number of dosages (e.g., capsules, tablets, suspensions, or other dosage form), usually six. The dissolution media is typically maintained at 37° C. during the test. It is noted that if the dosage form being tested is a capsule, 1% (w/w) of pancreatin or other source of trypsin may need to be added to the phosphate buffer dissolution medium so that the capsule shell does not interfere with the test. The amount of dissolved ziprasidone can be determined conventionally by HPLC, as hereinafter described.

The term "particles" refers to individual particles whether the particles exist singly or are agglomerated. Thus, a composition comprising particulate ziprasidone hydrochloride may contain agglomerates that are well beyond the size limit of about 85 μm specified herein. However, if the mean size of the primary drug substance particles (i.e., ziprasidone free base or ziprasidone hydrochloride) comprising the agglomerate are less than about 85 μm individually, then the agglomerate itself is considered to satisfy the particle size constraints defined herein and the composition is within the scope of the invention.

Reference to ziprasidone free base or to ziprasidone hydrochloride particles having "a mean particle size" (herein also used interchangeably with "VMD" for "volume mean diameter") equal to or less than a given diameter or being within a given particle size range means that the average of all ziprasidone particles in the sample have an estimated volume, based on an assumption of spherical shape, less than or equal to the volume calculated for a spherical particle with a diameter equal to the given diameter. Particle size distribution can be measured by Malvern light scattering as known to those skilled in the art and as further disclosed and discussed below.

"Bioequivalent" as employed herein means that if a dosage form comprising crystalline ziprasidone particles and a pharmaceutically acceptable carrier, said particles having a given mean particle size, is tested in a crossover study (usually comprising a cohort of at least 10 or more human subjects), the average Area under the Curve (AUC) and/or the $C_{max}$ for each crossover group is at least 80% of the (corresponding) mean AUC and/or $C_{max}$ observed when the same cohort of subjects is dosed with an equivalent formulation differing only in that the ziprasidone particle size is 20 microns ($\mu$m), preferably with a $D_{90}$ of about 40 $\mu$m. The 20 $\mu$m particle size is, in effect, a standard against which other different formulations can be compared. AUCs are plots of serum concentration of ziprasidone along the ordinate (Y-axis) against time for the abscissa (X-axis). Generally, the values for AUC represent a number of values taken from all the subjects in a patient population and are, therefore, mean values averaged over the entire test population. $C_{max}$, the observed maximum in a plot of serum level concentration of ziprasidone (Y-axis) versus time (X-axis) is likewise an average value.

Use of AUCs, $C_{max}$, and crossover studies is, of course otherwise well understood in the art. The invention can indeed be viewed in alternative terms as a composition comprising crystalline ziprasidone particles having a mean particle size equal to or less than about 85 $\mu$m, as measured by Malvern light scattering, and a pharmaceutically acceptable carrier, said composition exhibiting a mean AUC and/or mean $C_{max}$ which are at least 80% of the corresponding mean AUC and/or $C_{max}$ values exhibited by a composition equivalent thereto (i.e., in terms of excipients employed and the amount of ziprasidone hydrochloride) but having a ziprasidone mean particle size of 20 $\mu$m. Use of the term "AUC" for purposes of this invention implies crossover testing within a cohort of at least 10 healthy subjects for all compositions tested, including the "standard" 20 $\mu$m particle size composition.

DETAILED DESCRIPTION

As previously stated, ziprasidone free base or ziprasidone hydrochloride in any form which will crystallize can be used in this invention, including anhydrous or, in the case of the hydrochloride, ziprasidone hydrochloride monohydrate. The ziprasidone hydrochloride employed herein, including the examples, was ziprasidone hydrochloride monohydrate, and is generally referred to throughout simply as ziprasidone hydrochloride for convenience. Crystalline ziprasidone free base itself can be formed from the hydrochloride by adding or titrating a base (for example an alkali metal hydroxide such as sodium hydroxide) to a suspension of the acid addition salt in water, usually with stirring. Base is added at a rate such that the pH preferably rises to at least about 5. A preferred pH range within which to conduct the neutralization is from about 5 to about 7. The neutralization reaction can take up to several hours or more, depending on the quantity of hydrochloride being neutralized, the volume employed, the concentration of base and so forth. The free base, being much less soluble at near-neutral pH than the acid addition salt, crystallizes out of solution as the neutralization progresses to completion. The neutralization end point occurs when the pH no longer swings acid following the addition of base, indicating that the acid has been consumed. If the particle size measured is not less than 85 $\mu$m, it can be milled to give material of intermediate or smaller particle size, as known in the art.

Alternatively the ziprasidone free base may be obtained directly via the synthesis described in U.S. Pat. No. 5,338, 846, herein incorporated by reference.

It will be appreciated by those skilled in the art of powder production that there are numerous known methods which can be applied to producing crystalline ziprasidone hydrochloride particles having a mean particle size equal to or less than about 85 $\mu$m. For example, the hydrochloride salt can be made by treating the free base with aqueous HCl, as generally described in U.S. Pat. No. 4,831,031. In particular, there are two preferred crystallization process options which have been utilized for the production of ziprasidone hydrochloride monohydrate crystals for the bioequivalence studies exemplified herein. The process which gives the smallest particle sizes, typically a VMD of about 5 to 30 $\mu$m, comprises suspending ziprasidone free base as a slurry in a mixture of tetrahydrofuran (THF) and water, where the major component of the solvent mixture is water, adding aqueous HCl to form the hydrochloride, and refluxing, usually for several hours depending on the scale (lab or production) being implemented. The ratio (v/v) of water to THF is typically 13–17 (water) to 0–5 (THF). This process has been described in U.S. Pat. No. 5,312,925, herein incorporated by reference. Due to the low solubility of ziprasidone, this process results in the conversion of the free base to the hydrochloride salt without ever obtaining a solution. The slurry requires a substantial reflux period to form the hydrochloride salt. The long reflux together with the low solubility results in smaller particle size when this process option is used.

A second preferred process option for making large crystalline particles involves crystallizing ziprasidone hydrochloride monohydrate from solution. A solution of the free base of ziprasidone is prepared in THF and water at (or near) reflux, where the mixture is predominantly THF, the volume ratio of THF to water typically being 22–35 (THF) to 1.5–8 (water), preferably 24–30 (THF) to 2–6 (water). Then the mixture is heated, preferably to a temperature just below reflux so that mechanical reduction of the crystals can be avoided, and an aqueous HCl solution is added to form the hydrochloride monohydrate salt. Once addition of the HCl solution is commenced, crystals form and start to drop out of solution. Since reflux temperature is usually about 65° C., typically a temperature of 60–64° C. is employed/maintained. Although it is generally desirable to avoid reflux for large crystal sizes, slow agitation such as slow stirring can be employed to even out temperature in the reaction vessel. Again, the length of time heating is applied will depend on the scale (e.g., benchtop or production) being implemented, but is typically anywhere from a few minutes to several hours. Once heating is completed, the reaction is cooled, preferably slowly over a period of typically at least 2 hours, preferably at least four hours at production scale, until room temperature is reached. This method was utilized to prepare several larger particle size lots. In general, enriching the solvent in THF will increase crystal particle size. Generally, large particles having a VMD of 50–150 μm can be produced by this method. It is noted that if a large particle size lot having a VMD greater than 85 μm is obtained, it can be milled to give material of intermediate or smaller particle size, and this constitutes yet another method of making particulate ziprasidone hydrochloride monohydrate crystals suitable for use in the invention.

When growing crystals toward the 85 μm end of the range, or larger, a number of factors are important for producing a large crystal size. First, high purity of the ingoing ziprasidone free base is helpful in growing larger crystals. Also, as it has been noted, conducting the crystallization just below reflux is helpful, and it is possible that dropping the temperature just below reflux decreases the amount of stress on the crystal. Additionally, using a slow rate of agitation further reduces crystal breakage. Use of dilute HCl solution in place of concentrated HCl further increases crystal size. Two factors which also have been found to be helpful for forming large crystals are (1) slowing the addition of the acid, and (2) having a stir period after an initial 10% acid charge, so that only a relatively few seed crystals are generated prior to the remaining HCl being charged. A detailed experimental procedure is presented in the Examples.

The process of preparing large ziprasidone HCl crystals as presented above is believed to be novel, and is accordingly provided as a further feature of the invention. Thus the invention provides a process of preparing large crystals of ziprasidone hydrochloride monohydrate, comprising the steps of:

1) dissolving ziprasidone free base in a solvent comprising THF and water, in a volume ratio of about 22–35 unit volumes of THF to about 1.5–8 volumes of water;
2) heating the solution resulting from step (1);
3) adding HCl to the solution resulting from step (2); and
4) cooling the solution resulting from step (3).

Once the solution has been cooled, The crystals can be harvested conventionally, for example by filtration, and dried.

Compositions comprising ziprasidone free base or ziprasidone hydrochloride having a mean particle size less than 85 μm can be formulated into conventional, usually dry, pharmaceutical dosage forms such as tablets, powders for oral suspension, unit dose packets, and capsules for oral adminstration, and such dosage forms can be made by conventional methodology. Ziprasidone free base can also be incorporated into a pre-constituted oral suspension as described in application No. 60/136,268, filed provisionally in the US of even date herewith, and herein incorporated by reference.

The compositions, in addition to ziprasidone free base or ziprasidone hydrochloride, can contain conventional pharmaceutically acceptable excipients such as, for example: fillers and diluents such as starches and sugars; binders such as carboxymethyl cellulose and other cellulose derivatives, alginates, gelatine, and polyvinyl pyrrolidone; disintegrating agents such as agar-agar, calcium carbonate and sodium bicarbonate, pregelatinized starch, sodium croscarmellose, sodium starch glycolate and crosslinked poly(vinyl pyrrolidone); lubricants such as talc, sodium lauryl sulfate, stearic acid, calcium and magnesium stearate, and solid polyethyl glycols. Some excipients can serve more than one function; for example, a disintegrant can also serve as a filler.

In a preferred manufacturing process embodiment, ziprasidone free base or ziprasidone hydrochloride monohydrate, lactose monohydrate and pregelatinized starch are first sieved or gently milled using common stainless steel sieves or mechanical mills in order to ensure that all components are de-lumped. The mixture is then blended for 30 minutes to ensure good homogeneity, for example using a tumbling blender such as a V-blender or a bin blender. Following blending, magnesium stearate (0.75% w/w) is added and blending is continued for five more minutes. The blended mixture is then added into the hopper of a roller compacter, then compacted and milled to form a granulation. The granulation is then further blended as described above for 10 minutes. Following blending additional lubricant (magnesium stearate, 0.5% w/w) is added and blending continued for an additional five minutes. The mixture can then be sampled if desired prior to, for example, encapsulating conventionally using, for example, an H&K or Bosch encapsulation machine.

Tablets can be made by conventional methodology and employing conventional equipment.

The amount of ziprasidone free base or ziprasidone hydrochloride contained in a tablet, capsule, or other dosage form containing a composition of this invention will usually be between 5 and 100 μmg, usually administered orally twice a day, although amounts outside this range and different frequencies of administration are feasible for use in therapy as well. As previously mentioned, such dosage forms are useful, inter alia, in the treatment of psychotic disorders, for example of the schizophrenic type, as disclosed in U.S. Pat . No. 4,831,031.

As noted, average particle size can be determined by Malvern light scattering, a laser light scattering technique. In the examples below, the particle size for ziprasidone HCl monohydrate drug substance was measured using a Malvern Mastersizer Model MS1 particle size analyzer (Malvern Instruments Inc., 10 Southville Rd., Southborough, Mass. 01772) with a Small Volume Recirculating unit attached. A 300RF mm lens and a beam length of 2.4 mm was used. A recirculating speed set to 11 o'clock was used to ensure that the sample remained suspended. Samples for analysis were prepared by adding a weighed amount of ziprasidone hydrochloride (500±10 mg) to a 16 mL glass vial. To this vial was added 10 mL of suspending media, specifically a previously prepared mixture of hexanes (ACS reagent grade) containing 1% Span 85. The ziprasidone hydrochloride was suspended by shaking well for approximately 5 seconds. 60 second sonication can be implemented to effectively break agglomerates and help suspend particles, if necessary. Prior to analysis of the sample, a background count was achieved by filling the measurement cell with 100 mL of the suspending media. For sample analysis, a disposable Pasteur pipette was used to first withdraw and empty portions of the suspension several times to ensure representative sampling of the sample vial contents. Then the pipette was filled and a few drops of the vial contents were added to the suspending medium in the measurement cell until an obscuration value of roughly 20% was obtained. This sampling procedure was performed while continuously shaking the vial to avoid settling of the suspension during sampling. Volume distributions were obtained and, for characterization, the values for $D_{10}$, $D_{50}$, $D_{90}$ and Volume Mean Diameter (VMD=D[4,3] were specifically listed (NOTE: Mean particle size values mentioned herein refer to measured VMD values). Upon measurement completion, the sample cell was emptied and cleaned, refilled with suspending medium, and the sampling procedure repeated for a total of three measurements.

A dosage form can be tested to assess its dissolution profile by dissolution testing it in a USP-2 apparatus. As previously described, the apparatus is implemented to contain 900 ml of 0.05 M $NaH_2PO_4$ buffer, pH 7.5, containing 2% (w/w) sodium dodecyl sulfate. 1% pancreatin may be added if the dosage form being tested is a capsule, as previously noted. The pH can be adjusted as approprate using, for example, 5N NaOH or concentrated phosphoric acid. The USP-2 apparatus is equipped with paddles stirring at 75 rpm. The dosage form (e.g., tablet or capsule) is added directly to the aqueous dissolution medium. If the dosage form is a capsule, it is inserted into a plastic clip (of the type available commercially as a Vankel, Part No. T-1045-8) to maintain the capsule at the bottom of the vessel during initial dissolution. The dissolution medium is typically maintained at 37° C. during the test. A dosage form is within the scope of the invention if at least 70% of the ziprasidone hydrochloride, preferably 75%, dissolves in the phosphate solution within 45 minutes.

The amount of dissolved ziprasidone can be determined conventionally by HPLC. As an example of an HPLC assay to determine ziprasidone solubility, the amount of dissolved ziprasidone can be determined by using a suitable chromatographic column such as a Zorbax® Rx $C_8$ Reliance (Mac-Mod Analytical Inc., 127 Common Court, PO Box 2600, Chadds Ford, Pa. 19317), 4.0×80 mm column with an isocratic mobile phase consisting of 45% acetonitrile and 55% 0.05 potassium dihydrogen phosphate buffer, pH 6.5, at a flow rate of 1.0 ml/min at 40° C. Detection can be by UV absorption at a wavelength of 215 nm. Quantification can be effected facilely by comparison of HPLC peak height (or area) with the peak height (or area) taken from a standard plot of concentration vs. peak height (or area) for standards of known concentration. As is conventional, the ziprasidone standard concentrations are selected to fall within a linear range of concentration vs absorbance for the UV detector employed.

The invention is further exemplified and disclosed by the following non-limiting examples:

EXAMPLE 1

To illustrate the invention, a human pharmacokinetic open, randomized, three period, two treatment crossover study at steady-state conditions with no wash-out period was conducted in which two ziprasidone capsule lots (identical compositions, identified in Table 1 as Example 3), each comprising 20 mg activity of ziprasidone but having different ziprasidone hydrochloride particle size, were administered to a total of 14 healthy subjects, both male (11 patients) and female (3 patients). Subjects were dosed orally twice daily (1×20 mg capsule, 12 hours apart) in the fed state immediately after consuming an identical breakfast or evening meal. Doses were administered with 50 ml of water. On the third day of each period (days 3, 6 and 9), each subject consumed a breakfast consisting of two eggs fried in butter, 2 strips of bacon, 6 ounces of hash brown potatoes, 2 pieces of toast with 2 pats of butter and 8 ounces of whole milk. Immediately following breakfast, 1×20 mg capsule was dosed, and blood samples withdrawn at the following times: 0 (just prior to dosing), 0.5, 1,2,3,4,6,8,10 and 12 hours. Additional serum samples were obtained prior to morning dosing on days 1, 2, 4, 5, 7 and 8. Serum ziprasidone concentration was determined using a high performance liquid chromatography assay along lines set forth in Janiszewski et al., J. Chromatography B: Biomedical applications, Jun. 9, 1995, 668 (1), pp.133–139, and can be described as follows:

Serum samples are prepared by weak action exchange on solid phase extraction (SPE) columns. Following conditioning of the SPE columns with methanol and aqueous acetic acid, 0.5 ml aliquots of serum are added to each SPE column followed by 0.05 ml of an internal standard, typically 20 ng per 50 $\mu$in 50% methanol/50% water. The samples are aspirated through the column by applying vacuum and washed with small amounts of reagents such as aqueous acetic acid, methanol and 0.25% triethylamine (TEA) in acetonitrile. The samples are then eluted into silanized glass test tubes with a single column volume of solvent such as 1.0% TEA in acetonitrile. After evaporating off the solvent (40° C. to 60° C. under $N_2$), the dried residues are reconstituted in 40 $\mu$l of mobile phase (2:1 deionized water/acetonitrile with 0.05% trifluoroacetic acid and 0.08% triethylamine) for which the pH is adjusted to 0.5 using concentrated HCl. After centrifugation, these samples are analyzed using a Supelco Supelcosil™ LC-18-DB narrow-bore column maintained at 35° C. utilizing a flow rate of 0.27 ml/min and UV absorption at 215 nm.

The mean particle sizes employed in the two capsule lots were 20 and 46 $\mu$m. Maximum observed serum ziprasidone concentrations ($C_{max}$) were estimated directly from the experimental data. $T_{max}$ (the time of first occurrence of $C_{max}$) was noted. The area under the serum ziprasidone concentration-time curve from 0 to 12 hours post dose ($AUC_{0-12}$) was estimated using linear trapezoidal approximation. Relative bioavailability was estimated from the ratio of adjusted steady state mean $AUC_{0-12}$ values comparing the 46 $\mu$m particle size to the 20 $\mu$m particle size.

Visual inspection of the data indicated steady-state systemic exposures were attained by day three. No apparent differences were noted in pharmaco-kinetic parameters between males and females. It is noted that only a limited assessment of gender effects could be made as only three of the 14 subjects participating in the study were women. $T_{max}$ values ranged from 0 to 12 hours, however, mean values ranged from 5 to 8 hours across all treatments. No statistically significant difference was observed for $T_{max}$ between the two treatments (p=0.63) and the adjusted mean $T_{max}$ values were 6.8 and 6.3 hours, respectively. Exposure (AUC) was similar for both particle sizes and the mean relative bioavailability for the 46 $\mu$m capsules (compared to the 20 $\mu$m capsules) was 100.2%. Similarly, the ratio of adjusted mean $C_{max}$ values comparing the 46 $\mu$m particle size to the 20 $\mu$m particle size was 96.6%. 90% confidence intervals were $AUC_{0-12}$ (89.1%, 112.7%) and $C_{max}$ (86.0%, 108.5%). Thus, 20 mg capsules prepared using a larger particle size (46 $\mu$m) provide equivalent systemic exposures to capsules prepared using the smaller particle size (20 $\mu$m).

EXAMPLE 2

This example is comparative and further demonstrates the effect of ziprasidone hydrochloride particle size on systemic exposure of ziprasidone dosed in a capsule dosage form.

Three lots of ziprasidone hydrochloride capsules containing 20 mg activity were manufactured (Example 3 listed in Table 1) each utilizing a different ziprasidone hydrochloride lot possessing a different particle size, specifically a mean particle size (VMD) of either 20 $\mu$m, 84 $\mu$m or 105 $\mu$m. The capsules containing the 20 $\mu$m ziprasidone hydrochloride were from the same capsule lot as described in Example 3.

The effect of particle size on ziprasidone bioavailability from these dosage forms was determined using an open, randomized, three period, three treatment, single-dose crossover human pharmacokinetic study consisting of eleven healthy subjects. Subjects were dosed orally (1×20 mg capsule) on days 1, 8 and 15 immediately after consuming a breakfast consisting of two eggs fried in butter, 2 strips of bacon, 2 ounces of hash brown potatoes, 2 pieces of toast with 2 pats of butter and 8 ounces of whole milk. Each dose was administered with 50 ml of water. Blood was then sampled at the following times: 0 oust prior to dosing), 1, 2, 3, 4, 6, 8, 12, 18, 24, and 36 hours after drug administration. For each subject after each dose, the area under the drug serum concentration vs. time curve ($AUC_{0-inf}$) and the maximum observed serum ziprasidone concentrations ($C_{max}$) were determined.

The ratios of average $AUC_{0-inf}$ and $C_{max}$ from dosing the capsules containing the larger sized ziprasidone hydrochloride (84 and 105 $\mu$m) relative to those average values obtained from dosing the capsules containing the smaller 20 $\mu$m ziprasidone hydrochloride were used as a measure of the effect of particle size on ziprasidone oral bioavailability. Average $AUC_{0-inf}$(84 $\mu$m)/$AUC_{0-inf}$(20 $\mu$m) and $C_{max}$(84 $\mu$m)/$C_{max}$(20 $\mu$m) were 81% and 90%, respectively. Average $AUC_{0-inf}$(105 $\mu$m)/$AUC_{0-inf}$(20 $\mu$m) and $C_{max}$(105 $\mu$m)/$C_{max}$ (20 $\mu$m) were 75% and 77%, respectively.

EXAMPLES 3–9

The following formulations are representative of those within the scope of the invention. All formulations were made by the preferred manufacturing process previously described using ziprasidone hydrochloride particles having a mean particle size between 20 and 85 $\mu$m. All formulations were used as capsule fill.

EXAMPLE 10

This example illustrates a procedure for making large crystals of ziprasidone hydrochloride monohydrate. Double recrystallized ziprasidone free base was selected for use in this procedure. The lot assayed at a purity of 99.7%.

A clean and dry glass-lined reactor was charged with 180 L of THF, 18 L of deionized water, and 6.0 Kg of ziprasidone free base. The slurry was heated to reflux, giving a clear solution. A HCl solution was prepared from 16 L of deionized water and 1.8 L of concentrated HCl in a separate charge tank. The agitator in the tank was set to the slow speed. The reactor was cooled to just below reflux (60–62° C., THF refluxes at ~64° C.) and an initial 2 Kg of the HCl solution were added. This brought the crystallization to the point of turbidity. The crystallization mixture was maintained at 62° C. for 30 minutes, thereby allowing seed crystals to develop. Following the stir period, the rest of the HCl solution was added over an additional 45 minute period. When the addition was complete, the slurry was slowly cooled from 62° C. to 13° C. to complete the crystallization. The product, ziprasidone hydrochloride monohydrate, was collected on a glass-lined enclosed pressure filter, and the cake was washed with 6 L of fresh cold THF.

The product was dried under vacuum at 25 to 35° C. to obtain the desired monhydrate (water content by Karl Fischer, KF=3.9 to 4.5%). 6.6 Kg of product was obtained, a 97% yield. The product showed a single peak by HPLC analysis (LOQ<0.05%) which matched the retention time of the standard.

The crystal size obtained was 105 $\mu$m, it being noted that this large crystal size can be milled to smaller sizes having a mean particle size less than 85 $\mu$m.

EXAMPLE 11

A suspension formulation was prepared by heating 733.31 g of water to 70° C. followed by adding 1.36 g methylparaben and 0.17 g propylparaben while stirring at about 200 rpm with an overhead stirrer. After the parabens completely dissolved, the temperature was lowered to about 30° C. The following components were then added in order: 2.78 g xanthan gum, 333.90 g xylitol, 1.13 g anhydrous citric acid,

TABLE 1

| Example No. | 3 (a) (mg/capsule) | 4 (a) (mg/capsule) | 5 (b) (mg/capsule) | 6 (a) (mg/capsule) | 7 (a) (mg/capsule) | 8 (a) (mg/capsule) | 9 (a) (mg/capsule) |
|---|---|---|---|---|---|---|---|
| Ziprasidone Hydrochloride Monohydrate, Pfizer | 22.65[c] | 45.30[c] | 21.76 (a) | 22.65[c] | 67.95[c] | 90.60[c] | 113.25[c] |
| Lactose Monohydrate, Ph. Eur. | 66.10[e] | 87.83[e] | 245.24[e] | 66.10[e] | 131.74[e] | 175.65[e] | 219.56[e] |
| Pregelatinized Maize Starch, BP | 10.00 | 15.00 | 30.00 | 10.00 | 22.50 | 30.00 | 37.50 |
| Magnesium Stearate, Ph. Eur. | 0.75 | 1.12 | 3.00 | 0.75 | 2.81 | 3.75 | 4.69 |
| Magnesium Stearate, Ph. Eur. | 0.50 | 0.75 | — | 0.50 | | | |
| Hard Gelatin, Locking Capsule Shell, Pharm[f] | Size #4 Blue/White | Size #4 Blue/Blue | Size #2 Black/Blue | Size #4 Blue/Blue | #3 White/White | #2 Blue/White | #1 Blue/Blue |
| TOTAL (mg/capsule) | 100.00 | 150.00 | 300.00 | 100.00 | 225.00 | 300.00 | 375.00 |

[a]Manufactured by dry granulation process.
[b]Manufactured by direct fill process.
[c]Based on a theoretical potency factor of 88.3%.
[d]Based on a potency factor of 91.9%.
[e]The lactose monohydrate weight is adjusted according to small potency changes in the ziprasidone hydrochloride monohydrate in order to maintain a constant capsule weight.
[f]Capsule shell color may be varied if needed, and does not impact capsule performance.

1.21 g trisodium citrate dihydrate, 0.55 g polysorbate 80, 11.13 g NaCl, 11.33 g ziprasidone hydrochloride monohydrate having a nominal particle size of 38 $\mu$m, 11.13 g colloidal silicon dioxide, and 5.0 g cherry flavor. The pH was adjusted to 4.0 using aqueous sodium hydroxide and hydrochloric acid as needed.

EXAMPLE 12

This example discloses a process for making a ziprasidone free base suspension.

Into a 2 liter beaker was weighed 812.9 g of water which was stirred using an overhead stirrer at a speed of about 200 rpm. The water was heated to 70° C. Once the temperature reached 70° C., 1.36 g of methylparaben and 0.17 g of propylparaben were added. When the parabens were completely dissolved, the temperature was lowered to 40° C. To the solution was slowly added 3.27 g of a viscosity agent, CARBOPOL® resin 974P (Union Carbide Corporation, Danbury, Conn.), taking care to avoid big lumps, and increasing the stirring speed as necessary. Agitation was maintained until the viscosity agent had completely dispersed and/or dissolved. To the solution was added 218 g of sucrose. After dissolving the sucrose, temperature was lowered to 30° C. To the solution was added 2.94 g of trisodium citric salt. To the solution was added 0.544 g of polysorbate 80. To the solution was slowly added 11.325 g of ziprasidone free base. A 10% NaOH solution was used to adjust the pH of the formulation to 5.7. After the pH had equilibrated, 1.09 g of colloidal silicon dioxide (CAB-O-SIL®, Cabot Corporation) was added.

What is claimed is:

1. A composition comprising crystalline ziprasidone free base or crystalline ziprasidone hydrochloride particles having a mean particle size equal to or less than about 85 μm and a pharmaceutically acceptable diluent or carrier.

2. A composition as defined in claim 1, wherein said composition comprises ziprasidone hydrochloride monohydrate.

3. A composition as defined in claim 1, wherein said mean particle size is equal to or less than 50 μm.

4. A composition as defined in claim 3, wherein said mean particle size is from 5 to 50 μm.

5. A composition as defined in claim 4, wherein said mean particle size is from 5 to 40 μm.

6. A composition as defined in claim 5, wherein said mean particle size is from 5 to 30 μm.

7. A composition as defined in claim 1 which exhibits an AUC and/or $C_{max}$ that is at least 80% of the mean AUC and/or $C_{max}$ observed for an equivalent formulation differing only in that the ziprasidone hydrochloride mean particle size is 20 μm.

8. A composition as defined in claim 1, wherein, when an amount of said dosage form equivalent to 100 mgA or less of ziprasidone is placed in a USP-2 apparatus containing 900 ml of aqueous $NaH_2PO_4$ buffer, pH 7.5, containing 2% (w/v) sodium dodecyl sulfate, and equipped with paddles stirring at 75 rpm, at least 70% of the ziprasidone therein dissolves within 45 minutes.

9. A method of treating a psychosis, comprising administering to a patient in need of such treatment an effective amount of a composition as defined in claim 1.

10. A method as defined in claim 9, wherein said composition comprises ziprasidone hydrochloride monohydrate.

11. A method as defined in claim 9, wherein said mean particle size is equal to or less than 50 μm.

12. A method as defined in claim 11, wherein said mean particle size is from 5 to 50 μm.

13. A method as defined in claim 12, wherein said mean particle size is from 5 to 40 μm.

14. A method as defined in claim 13, wherein said mean particle size is from 5 to 30 μm.

15. A method as defined in claim 9 wherein said composition exhibits an AUC and/or $C_{max}$ that is at least 80% of the mean AUC and/or $C_{max}$ observed for an equivalent composition differing only in that the ziprasidone hydrochloride particle size is 20 μm.

16. A method as defined in claim 9 wherein, when an amount of said composition equivalent to 100 mgA or less of ziprasidone is placed in a USP-2 apparatus containing 900 ml of aqueous $NaH_2PO_4$ buffer, pH 7.5, containing 2% (w/v) sodium dodecyl sulfate, and equipped with paddles stirring at 75 rpm, at least 70% of the ziprasidone therein dissolves within 45 minutes.

17. A composition comprising crystalline ziprasidone free base or crystalline ziprasidone hydrochloride particles having a mean particle size equal to or less than about 85 μm, as measured by Malvern light scattering, and a pharmaceutically acceptable carrier, said composition exhibiting a mean AUC and/or $C_{max}$ which is at least 80% of the mean AUC exhibited by a composition equivalent thereto but differing only in that it has a crystalline ziprasidone hydrochloride mean particle size of 20 μm.

18. A composition as defined in clam 17, which comprises crystalline ziprasidone hydrochloride monohydrate.

19. A composition as defined in claim 17, wherein said mean particle size is equal to or less than 50 μm.

20. A composition as defined in claim 19, wherein said mean particle size is from 5 to 50 μm.

21. A composition as defined in claim 20, wherein said mean particle size is from 5 to 40 μm.

22. A composition as defined in claim 21, wherein said mean particle size is from 5 to 30 μm.

23. A composition as defined in claim 17, wherein, when an amount of said composition equivalent to 100 mgA or less of ziprasidone is placed in a USP-2 apparatus containing 900 ml of aqueous $NaH_2PO_4$ buffer, pH 7.5, containing 2% (w/v) sodium dodecyl sulfate, and equipped with paddles stirring at 75 rpm, at least 70% of the ziprasidone hydrochloride therein dissolves within 45 minutes.

24. A method of treating a psychosis, comprising administering to a patient in need of such treatment an effective amount of a composition as defined in claim 17.

25. A method as defined in claim 24, which comprises ziprasidone hydrochloride monohydrate.

26. A method as defined in claim 24, wherein said mean particle size is equal to or less than 50 μm.

27. A method as defined in claim 26, wherein said mean particle size is from 5 to 50 μm.

28. A method as defined in claim 27, wherein said mean particle size is from 5 to 40 μm.

29. A method as defined in claim 28, wherein said mean particle size is from 5 to 30 μm.

30. A method as defined in claim 24, wherein, when an amount of said composition equivalent to 100 mgA or less of ziprasidone is placed in a USP-2 apparatus containing 900 ml of aqueous $NaH_2PO_4$, pH 7.5, containing 2% (w/v) sodium dodecyl sulfate, and equipped with paddles stirring at 75 rpm, at least 70% of the ziprasidone therein dissolves within 45 minutes.

31. A process of preparing large crystals of ziprasidone hydrochloride monohydrate, comprising the steps of:

1) dissolving ziprasidone free base in a solvent comprising THF and water, in a volume ratio of about 22–35 unit volumes of THF to about 1.5–8 volumes of water;
2) heating the solution resulting from step (1);
3) adding HCl to the solution resulting from step (2); and
4) cooling the solution resulting from step (3).

32. A process as defined in claim 31, wherein the volume ratio of THF to water in said solvent is 24–30 to 2–6.

33. A process as defined in claim 31, wherein, in said step (3), the temperature of said solution is maintained below reflux.

34. A process as defined in claim 33, wherein said temperature is 60–64° C.

* * * * *